US011008563B2

(12) United States Patent
Kusakabe

(10) Patent No.: US 11,008,563 B2
(45) Date of Patent: May 18, 2021

(54) DRIED L-GLUTAMATE OXIDASE COMPOSITION

(71) Applicants: YAMASA CORPORATION, Choshi (JP); ENZYME-SENSOR Co., Ltd., Tsukuba (JP)

(72) Inventor: Hitoshi Kusakabe, Tsukuba (JP)

(73) Assignees: YAMASA CORPORATION, Choshi (JP); ENZYME-SENSOR CO., LTD., Tsukuba (JP)

( * ) Notice: Subject to any disclaimer, the term of this patent is extended or adjusted under 35 U.S.C. 154(b) by 103 days.

(21) Appl. No.: 16/200,897

(22) Filed: Nov. 27, 2018

(65) Prior Publication Data
US 2019/0161747 A1 May 30, 2019

(30) Foreign Application Priority Data

Nov. 29, 2017 (JP) .............................. JP2017-228920

(51) Int. Cl.
*C12N 9/96* (2006.01)
*C12N 9/06* (2006.01)

(52) U.S. Cl.
CPC ............. *C12N 9/96* (2013.01); *C12N 9/0022* (2013.01); *C12Y 104/03011* (2013.01)

(58) Field of Classification Search
None
See application file for complete search history.

(56) References Cited

U.S. PATENT DOCUMENTS

| 5,643,721 | A  | * | 7/1997 | Spring   | .................. | G01N 33/543 |
|           |    |   |        |          |                    | 435/6.16    |
| 6,294,365 | B1 | * | 9/2001 | De Rosier| ..............     | C12N 9/127  |
|           |    |   |        |          |                    | 435/188     |

FOREIGN PATENT DOCUMENTS

| CN | 1256442 A | 6/2000 | | |
| DE | 102009045798 A1 | * | 8/2010 | ............. A61Q 19/02 |
| EP | 10006640 A2 | 6/2000 | | |
| JP | 56-35985 A | 4/1981 | | |
| JP | 57-118790 A | 7/1982 | | |
| JP | 59-42896 A | 3/1984 | | |
| JP | 8-187095 A | 7/1996 | | |
| JP | 2006-42757 A | 2/2006 | | |
| JP | 2006-262865 A | 10/2006 | | |
| JP | 2011-120500 A | 6/2011 | | |
| JP | 2011-526492 A | 10/2011 | | |
| WO | 95/22057 A1 | 8/1995 | | |
| WO | 2010/035048 A1 | 4/2010 | | |

OTHER PUBLICATIONS

G0400, L-Glutamate Oxidase from *Streptomyces* sp., Sigma-Aldrich Catalog page, May 24, 2017 (Year: 2017).*
G0400-ProductSheet, Product Information Sheet for G0400) (Year: 2017).*
EC1.4.3.11, Information on EC 1.4.3.11, L-glutamate oxidase, BRENDA Entry, 2020 (Year: 2020).*
Sukhacheva, Extracellular L-Glutamate Oxidase of *Streptomyces* sp. Z-11-6: Obtainment and Properties, Microbiology, vol. 69, No. 1, 2000, pp. 17-20. Translated from Mikrobiologiya, vol. 69, No. 1, 2000 (Year: 2000).*
Prestrelski, Separation of Freezing- and Drying-Induced denaturation of lyophilized proteins using Stress-specific stabilization, Archives of Biochemistry and Biophysics, vol. 303, No. 2, June, pp. 465-473, 1993 (Year: 1993).*
Lactose, Lactose Pubchem Entry, 2020 (Year: 2020).*
Trehalose, Trehalose Pubchem Entry, 2020 (Year: 2020).*
Shariat et al., Protection of lactoperoxidase activity with sugars during lyophilization and evaluation of its antibacterial properties, Research in Pharmaceutical Sciences, Apr. 2015; 10(2): 152-160 (Year: 2015).*
Arima et al., Recombinant Expression, Biochemical Characterization and Stabilization through Proteolysis of an L-Glutamate Oxidase from *Streptomyces* sp. X-119-6, J. Biochem. 134, 805-812 (2003) (Year: 2003).*
Wang, Lyophilization and development of solid protein pharmaceuticals, International Journal of Pharmaceutics 203 (2000) 1-60 (Year: 2000).*
Lorenzen, E. et al., "Trehalose and Sorbitol Alter the Kinetic Pattern of Inactivation of Glutamate Dehydrogenase During Drying in Levitated Microdroplets", Journal of Pharmaceuticals Sciences, Dec. 1, 2013, vol. 102, No. 12, pp. 4268-4273, XP55561431; cited in EESR dated Mar. 7, 2019.
Extended European Search Report dated Mar. 7, 2019, issued in counterpart EP Application No. 18208482.2. (8 pages).
Office Action dated Feb. 3, 2020, issued in counterpart EP application No. 18208482.2. (3 pages).
Kusakabe et al., "Purification and Properties of a New Enzyme, L-Glutamate Oxidase, from *Streptomyces* sp. X-119-6 Grown on Wheat Bran", Agric. Biol. Chem., 1983, 47(6), pp. 1323-1328, cited in the specification (7 pages).
Kusakabe et al., "Methods for Determining L-Glutamate in Soy Sauce with L-Glutamate Oxidase", Agric. Biol. Chem., 1984, 48(1), pp. 181-184, cited in the specification (4 pages).
Yamauchi et al., "Determination of L-Glutamate in Soy Sauce with L-Glutamate Oxidase", Journal of Japan Soy Sauce Research Institute, 1987, Vo. 13, No. 1, pp. 8-12, cited in the specification (3 pages).

(Continued)

*Primary Examiner* — Louise W Humphrey
*Assistant Examiner* — Srikanth Patury
(74) *Attorney, Agent, or Firm* — Westerman, Hattori, Daniels & Adrian, LLP

(57) ABSTRACT

There is provided a dried L-glutamate oxidase composition containing an L-glutamate oxidase, which is stable even if it is stored for such a long term as one year or longer. The composition is a dried composition, preferably lyophilized product, containing an L-glutamate oxidase and a disaccharide. A preferred example of the disaccharide is lactose. Content of the disaccharide per 100 U of the L-glutamate oxidase is preferably 0.5 to 50 mg.

15 Claims, 1 Drawing Sheet

(56) References Cited

OTHER PUBLICATIONS

Yamauchi wt al., "Enzyme Electrode for Specific Determination of L-Glutamate", Third European Congress on Biolechnology, 1984, vol. I, pp. 705-710, cited in the specification (6 pages).
Notification of Reasons for Refusal dated Jan. 23, 2018, issued in counterpart Japanese Patent Application No. 2017-228920, w/English translation (6 pages).

\* cited by examiner

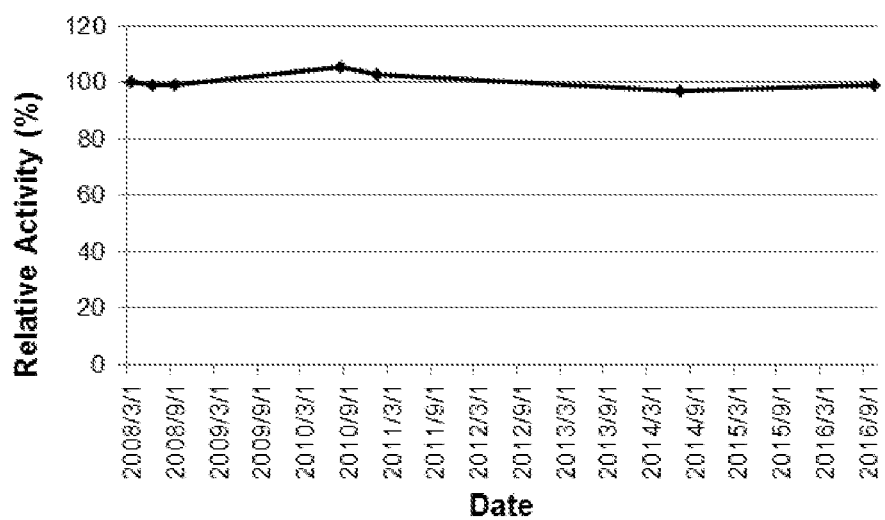

DRIED L-GLUTAMATE OXIDASE COMPOSITION

TECHNICAL FIELD

The present invention relates to a dried composition containing an L-glutamate oxidase and a disaccharide.

BACKGROUND ART

L-Glutamic acid is known as one of "umami" ingredients, and sodium L-glutamate as sodium salt thereof is used as a main ingredient of umami seasonings. L-Glutamic acid is also functioning as an excitatory neurotransmitter that causes neural transmission via the glutamate receptor in the bodies of animals. Therefore, detection and quantification of L-glutamic acid are extremely important in the fields of food science and biochemistry.

The applicants of the present application already found in 1983 through search and researches of oxidase enzymes of amino acids that one species of bacterium of the genus *Streptomyces* produces an L-glutamate oxidase that acts in an L-glutamic acid-specific manner (Non-patent document 1), and succeeded in commercial production thereof as a reagent for research. They further developed a method enabling easy measurement of L-glutamic acid using this enzyme, and put an L-glutamic acid measurement kit based on the method on the market (Non-patent documents 2 and 3). They also introduced an L-glutamic acid sensor using the L-glutamate oxidase immobilized on an oxygen electrode (Non-patent document 4). Thanks to these product developments and researches, colorimetric measurement kits and biosensors using L-glutamate oxidase have come to be widely used, and L-glutamate oxidase has come to have extremely high industrial value.

Raw material enzymes used for the kits or sensors are generally distributed as dried compositions in many cases. This is because they have advantages that, for example, the products are light and have a small volume, therefore they are suitable for storage and transportation, there is no risk about decomposition thereof by microbial contamination, dissolution concentration or type of buffer used at the time of dissolution thereof can be freely chosen according to the purpose of use, and they are more stable compared with a solution.

In the meantime, some enzymes have a problem that the activities thereof are reduced if they are in a state of low concentration solution or in the presence of high concentration of coenzyme, and means for stabilizing such enzymes have been examined. For example, there is an example that a saccharide or sugar alcohol is added to β-D-galactosidase (Patent document 1). In Patent document 1, a stability test of lyophilized products containing 18 kinds of saccharides or sugar alcohols is carried out, and it is described that residual activities of the enzyme observed after leaving the lyophilized products for two weeks at room temperature were around 85%. There are also known, for example, addition of (1) α-ketoglutaric acid, and/or L-glutamic acid, and/or (2) one or two or more kinds of compounds selected from the group consisting of a saccharide, a sugar alcohol, an amino acid or a salt thereof, and an organic acid or a salt thereof to a glutamate dehydrogenase in the presence of NADH or NADPH (Patent document 2), addition of one or more kinds of compounds selected from the group consisting of a saccharide, a sugar alcohol, an amino acid, an oligopeptide, and a protein, and/or a surfactant to a lactate oxidase (Patent document 3), addition of at least one kind of compound selected from the group consisting of bovine serum albumin, a saccharide, and an amino acid to a cholesterol oxidase (Patent document 4), and so forth.

PRIOR ART REFERENCES

Patent Documents

Patent document 1: Japanese Patent Unexamined Publication (KOKAI) No. 57-118790
Patent document 2: Japanese Patent Unexamined Publication (KOKAI) No. 56-035985
Patent document 3: Japanese Patent Unexamined Publication (KOKAI) No. 2011-120500
Patent document 4: Japanese Patent Unexamined Publication (KOKAI) No. 08-187095

Non-Patent Documents

Non-patent document 1: Agric. Biol. Chem., 47(6); 1323, 1983
Non-patent document 2: Agric. Biol. Chem., 48(1); 181, 1984
Non-patent document 3: Journal of Japan Soy Sauce Research Institute, 13(1); 8, 1987
Non-patent document 4: Third European Congress on Biotechnology, Vol. I, p. 705, 1984

SUMMARY OF THE INVENTION

Object to be Achieved by the Invention

However, it is difficult to previously predict how much degree of stabilization effect can be obtained with a combination of an objective enzyme and a stabilizer, and the actual condition is that search for such a stabilizer is performed on an empirical basis. As for L-glutamate oxidase, although lyophilized products thereof have been distributed so far, compounds to be added as a stabilizer have not been examined, and it has not been elucidated which compound is optimal as the stabilizer.

Therefore, an object of the present invention is to provide a highly stable dried L-glutamate oxidase composition containing an L-glutamate oxidase and a stabilizer. In order to industrially use such a composition, it is required to stably show, even after storage for a long period of time of 1 year or longer, the activity corresponding to, for example, 90% or more of the activity observed before the storage.

Means for Achieving the Object

The inventors of the present invention examined various substances in order to improve storage stability of dried L-glutamate oxidase composition. As a result of various researches, they found that disaccharides have superior ability to improve the storage stability, while sugar alcohols and polysaccharides do not show such an ability of desired level as the stabilizer, and therefore disaccharides are most suitable as the stabilizer, and accomplished the present invention.

That is, the present invention can be embodied as follows.

The present invention relates to a dried L-glutamate oxidase composition, which contains an L-glutamate oxidase and a disaccharide.

The present invention also relates to a dried L-glutamate oxidase composition, which contains an L-glutamate oxidase and lactose.

The present invention also relates to a lyophilized L-glutamate oxidase composition (i.e. a freeze-dried L-glutamate oxidase composition), which contains an L-glutamate oxidase and a disaccharide.

The present invention also relates to a lyophilized L-glutamate oxidase composition, which contains an L-glutamate oxidase and lactose.

The present invention also relates to such a dried or lyophilized L-glutamate oxidase composition as mentioned above, wherein the L-glutamate oxidase is derived from Streptomyces sp. X-119-6 (ATCC 39343).

The present invention also relates to such a dried L-glutamate oxidase composition or lyophilized L-glutamate oxidase composition as mentioned above, which contains 0.5 to 50 mg of the disaccharide per 100 U of the L-glutamate oxidase.

The present invention also relates to a dried L-glutamate oxidase composition, which contains an L-glutamate oxidase and a disaccharide, and shows, after storage for one year under frozen conditions of −20° C., an activity value of the enzyme corresponding to 95% or more of the activity value observed before the storage as measured by the MBTH method.

The present invention also relates to a dried L-glutamate oxidase composition, which contains an L-glutamate oxidase and lactose, and shows, after storage for one year under frozen conditions of −20° C., an activity value of the enzyme corresponding to 95% or more of the activity value observed before the storage as measured by the MBTH method.

The present invention also relates to a method for improving storage stability of an L-glutamate oxidase, which comprises dehydrating an aqueous composition containing the L-glutamate oxidase and a disaccharide, preferably lactose, to make the composition into a dried composition containing the L-glutamate oxidase and the disaccharide, preferably lactose.

The present invention also relates to a method for producing such a composition as mentioned above, which comprises preparing an aqueous composition containing the L-glutamate oxidase and a disaccharide, and dehydrating the prepared aqueous composition, to make the composition into a dried composition containing the L-glutamate oxidase and the disaccharide.

The present invention also relates to such a method as mentioned above, wherein the dehydrating step is carried out by lyophilizing to obtain a lyophilized product.

The present invention also relates to such a method as mentioned above, wherein the disaccharide is lactose.

The present invention also relates to such a method as mentioned above, wherein the aqueous composition comprises 0.5 to 50 mg of the disaccharide per 100 U of the L-glutamate oxidase.

The present invention also relates to such a method as mentioned above, further comprising producing the L-glutamate oxidase by a wild strain having an L-glutamate oxidase, or a cell obtained by transformed Escherichia coli or a actinomycete with a foreign L-glutamate oxidase gene.

The present invention also relates to such a method as mentioned above, wherein the aqueous composition is buffered in a pH range of 6.5 to 8.0.

The present invention also relates to such a method as mentioned above, wherein the concentration of a buffering agent in the buffered aqueous composition is 100 mM or lower.

Effect of the Invention

The dried composition of the present invention can show, after storage for two weeks at 37° C., an activity value of the enzyme corresponding to 90% or more, preferably 95% or more, more preferably 97% or more, of the activity value observed before the storage. Alternatively, the dried composition of the present invention can show, after storage for 4 weeks at −20° C., an activity value corresponding to 90% or more, preferably 95% or more, more preferably 97% or more, of the activity value observed before the storage. Alternatively, the dried composition of the present invention can show, after storage for 1 year at −20° C., an activity value corresponding to 90% or more, preferably 95% or more, more preferably 97% or more, of the activity value observed before the storage. Alternatively, the dried composition of the present invention can show, after storage for 5 year at −20° C., an activity value corresponding to 90% or more, preferably 95% or more, more preferably 97% or more, of the activity value observed before the storage. Alternatively, the dried composition of the present invention can show, after storage for 8 years at −20° C., an activity value corresponding to 90% or more, preferably 95% or more, more preferably 97% or more, of the activity value observed before the storage.

According to the present invention, handling of a dried composition of L-glutamate oxidase, especially such a lyophilized product, can be made easier.

BRIEF DESCRIPTION OF THE DRAWING

FIG. 1 shows change of activity value of a lyophilized L-glutamate oxidase composition containing lactose stored under −20° C. conditions.

MODES FOR CARRYING OUT THE INVENTION

The present invention relates to a dried L-glutamate oxidase composition, which contains an L-glutamate oxidase and a disaccharide.
[Dried Composition]
(L-Glutamate Oxidase)

L-Glutamate oxidase is an enzyme that catalyzes the following reaction.

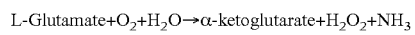

The L-glutamate oxidase used for the present invention is not particularly limited so long as it has a sufficient degree of the objective activity, and various L-glutamate oxidases can be used. A preferred example is the L-glutamate oxidase derived from Streptomyces sp. X-119-6 (ATCC 39343), which is disclosed in Japanese Patent Publication (KOKOKU) No. 61-26357.
(Disaccharide)

According to the examination performed by the inventors of the present invention, if a dried L-glutamate oxidase product contains a disaccharide, the activity of L-glutamate oxidase can be stably maintained during a storage period. Example of the disaccharide used for the present invention in order to obtain such an effect include sucrose, lactulose, lactose, maltose, trehalose, cellobiose, kojibiose, nigerose, isomaltose, isotrehalose, neotrehalose, sophorose, laminaribiose, gentiobiose, turanose, maltulose, paratinose, gentiobiulose, mannobiose, melibiose, melibiulose, neolactose, galactosucrose, scillabiose, rutinose, rutinulose, vicianose, xylobiose, primeverose, and so forth. Among the aforementioned disaccharides, those that do not affect the enzymatic reaction, and shows good solubility at a comparatively low temperature and pH at which L-glutamate oxidase is stable, for example, sucrose, lactose, maltose, trehalose, cellobiose, and isomaltose, are preferred, lactose and maltose are more preferred, and lactose is still more preferred. As the disaccharide, a mixture of two or more kinds of disaccharides may be used.

(Other Ingredients)

Besides the aforementioned L-glutamate oxidase and disaccharide, the dried composition of the present invention may contain one or two or more kinds of other additives such as excipients, buffering agents, dissolving aids, preservatives, and antiseptics.

The dried composition of the present invention may contain another excipient besides the disaccharide added in order to stabilize the activity of L-glutamate oxidase. Examples of such an excipient other than disaccharide include glucose, maltitol, mannitol, ribose, xylose, galactose, sorbitol, maltotriose, fructose, dextran, polyvinylpyrrolidone, methylcellulose, Ficoll, polyethylene glycol, polyvinyl alcohol, bovine serum albumin, collagen peptide, and so forth. The dried composition may also contain phosphate, citrate, acetate, or the like as a buffering agent.

(Content)

The L-glutamate oxidase is preferably contained in the dried composition of the present invention in an amount of 0.1 to 60 mass %, more preferably 1 to 30 mass %, still more preferably 5 to 15 mass %.

The disaccharide is preferably contained in the dried composition of the present invention in an amount of 1 to 95 mass %, more preferably 10 to 80 mass %, still more preferably 50 to 75 mass %. This is because if the disaccharide content is within these ranges, sufficient stabilizing effect can be obtained, and favorable physical properties of the dried composition can be obtained.

The amount of the disaccharide contained in the dried composition can be 0.10 to 150 mg per 100 U of the L-glutamate oxidase. In order to make it possible to stabilize the L-glutamate oxidase for a longer period of time, the amount is preferably 0.50 mg or more, more preferably 1.0 mg or more, still more preferably 1.6 mg or more, per 100 U of the L-glutamate oxidase. Disaccharides have a hygroscopic property, and therefore in order to favorably maintain the dried state of the composition, amount of the disaccharide contained in the dried composition is preferably 50 mg or less, more preferably 30 mg or less, still more preferably 15 mg or less, per 100 U of the glutamate oxidase.

(Dried Composition)

When the term "dried composition" is used for a composition containing L-glutamate oxidase in this specification, it means a composition in a dried state obtained by drying a solution dissolving at least an L-glutamate oxidase and a disaccharide, and it is not a composition obtained by simply mixing the L-glutamate oxidase in a dried state not containing the disaccharide and the disaccharide in a dried state not containing the L-glutamate oxidase. The dried L-glutamate oxidase composition can be put in another way with "dried composition of a solution (of L-glutamate oxidase and disaccharide)".

The dried composition of the present invention may be a spray-dried dried composition, or may be a lyophilized composition.

The features of the "dried composition" or "dried composition of a solution (of L-glutamate oxidase and disaccharide)" cannot be directly specified with structure or characteristics of the composition. First, when the dried composition is prepared, the solvent is removed from a solution of L-glutamate oxidase dissolved together with the disaccharide, and it is thought that, at this time, they come to be in a state that the disaccharide, of which molecule is smaller than that of the L-glutamate oxidase, bonds to the circumference and inside of the conformation of the L-glutamate oxidase molecule. There is no expression for clearly defining such a state with distinguishing it from a state obtained by simply mixing the L-glutamate oxidase in a dried state and the disaccharide in a dried state, which have been separately prepared. Further, it can be said that it is impossible to define such a state with results of instrumental analysis on the basis of the general state of the art of those skilled in the art at the time of the filing of this application.

(Features of Composition, and Others)

According to the examination of the inventors of the present invention, if an L-glutamate oxidase is made into a dried product together with a disaccharide, the activity thereof is maintained even after storage for a long period of time. Therefore, as another aspect of the present invention, there is provided a dried L-glutamate oxidase composition containing an L-glutamate oxidase and a disaccharide, wherein activity of the L-glutamate oxidase is stabilized. The expression "activity is stabilized" means that, after storage of the composition at 37° C. for 2 weeks, the activity value is 90% or more, preferably 95% or more, more preferably 97% or more, of the activity value observed before the storage. Alternatively, the expression means that, after storage of the composition at −20° C. for 4 weeks, the activity value is 90% or more, preferably 95% or more, more preferably 97% or more, of the activity value observed before the storage. Further alternatively, the expression means that, after storage of the composition at −20° C. for 1 year, the activity value is 90% or more, preferably 95% or more, more preferably 97% or more, of the activity value observed before the storage. Further alternatively, the expression means that, after storage of the composition at −20° C. for 5 years, the activity value is 90% or more, preferably 95% or more, more preferably 97% or more, of the activity value observed before the storage. Further alternatively, the expression means that, after storage of the composition at −20° C. for 8 years, the activity value is 90% or more, preferably 95% or more, more preferably 97% or more, of the activity value observed before the storage.

The enzymatic activity of L-glutamate oxidase can be measured by the oxygen electrode method or the MBTH method as described later. Degree of the stabilization of L-glutamate oxidase will be expressed on the basis of values measured by the MBTH method, unless especially indicated.

According to the examination of the inventors of the present invention, the effect of stabilizing L-glutamate oxidase obtainable with a disaccharide is stronger than that obtainable with a polysaccharide or sugar alcohol. Specifically, when one of polysaccharides, dextran, which is comparatively frequently used as a stabilizer at the time of lyophilization of proteins, was used in a dried L-glutamate oxidase composition, it provided a residual activity of 83.1% after storage under predetermined conditions, which is comparable to those obtainable by the methods for stabilizing carbohydrate-related enzymes using existing saccharides, and this degree of the stabilization was not improved even if the amount of dextran to L-glutamate oxidase was changed, so far as the inventors of the present invention examined. When one of sugar alcohols, mannitol, was used for a dried L-glutamate oxidase composition, the activity was halved after storage under predetermined conditions, and thus it did not give the stabilization effect.

Patent document 1 mentioned above proposes addition of a saccharide or sugar alcohol for stabilization of β-D-galactosidase, and the activity values of the enzyme observed for lyophilized products of the enzyme containing each of 18 kinds of saccharides or sugar alcohols reduced to around 85% after storage at room temperature for two weeks. According to the descriptions of Patent document 1 mentioned above, it is understood that the substances that showed a comparatively high degree of the objective effect among those used for β-D-galactosidase are sugar alcohols (specifically, sorbitol, mannitol, and inositol). However, it can be said that this effect of stabilizing β-D-galactosidase differs from the effect of stabilizing L-glutamate oxidase obtained with a disaccharide and disclosed in this application. Therefore, it can be said that the effect of stabilizing L-glutamate oxidase obtained with a disaccharide, especially lactose, is an effect disclosed for the first time by this application, which is hardly expected from the conventional techniques.

[Method for Producing Dried Composition]

The dried composition of the present invention can be produced by a production method comprising the step of preparing an aqueous composition containing an L-glutamate oxidase and a disaccharide, and the step of dehydrating the prepared aqueous composition to obtain a dried composition.

(Step of Obtaining Aqueous Composition)

The aqueous composition containing an L-glutamate oxidase and a disaccharide can be prepared by, for example, adding a disaccharide to a solution containing an L-glutamate oxidase, although the order of addition is not particularly limited. The term "aqueous composition" refers to a liquid composition that contains an ingredient in an aqueous solvent (for example, water).

The L-glutamate oxidase can be produced by a known method, for example, the methods described in Non-patent document 1 and WO2001/079503. The production host may be a wild strain having an L-glutamate oxidase, or may be cells obtained by transforming a host suitable for production such as *Escherichia coli* and actinomycetes with a foreign L-glutamate oxidase gene. Efficient production using an expression vector and production of the enzyme binding a fusion protein or the like are also possible. The culture conditions of L-glutamate oxidase-producing cells such as types of carbon source and nitrogen source, aeration conditions, and stirring conditions are not particularly limited. Culture conditions suitable for the host to be used can be used. In order to obtain an L-glutamate oxidase, cell collection using membrane separation or centrifugation, and purification and isolation consisting of a combination of cell disruption by ultrarsonication, French press treatment, or lysozyme treatment, heat treatment, salting out with ammonium sulfate, dialysis, treatment with a solvent such as ethanol, various chromatography techniques, and so forth can also be performed as required.

pH of the aqueous composition containing an L-glutamate oxidase and a disaccharide may be adjusted by adding a buffering agent. As the buffering agent, one showing a buffering ability in a pH range of 5.5 to 9.0 can be preferably used. A buffering agent the ingredients of which are not volatilized in the following drying step is preferred. Examples of such a buffering agent include such buffering agents as boric acid, Tris-hydrochloric acid, and potassium phosphate, as well as Good buffering agents such as ACES, BES, bicine, Bis-Tris, CHES, EPPS, HEPES, HEPPSO, MES, MOPS, MOPSO, PIPES, POPSO, TAPS, TAPSO, TES, and tricine. Examples also include buffering agents based on dicarboxylic acid such as phthalic acid, maleic acid, and glutaric acid. Among these, only one kind of buffering agent may be used, or two or more kinds of them may be used. The buffering agent may also be a complex composition of one or more kinds of compounds including a compound other than those mentioned above. A chelating agent such as EDTA, and a surfactant may be further added, as required. These can be prepared by using various commercially available reagents.

In a preferred embodiment, the aqueous composition containing an L-glutamate oxidase and a disaccharide is buffered with potassium phosphate. The pH thereof is preferably 6.5 to 8.0, more preferably 7.0 to 7.8. Concentration of the buffer is preferably comparatively low, in order to avoid influence thereof on stability of proteins at the time of concentration in the following drying step, and avoid lowering of the critical temperature of frozen solution at the time of lyophilization. The concentration is, for example, 100 mM or lower, preferably 50 mM or lower. Although the lowest concentration of the buffer is not particularly limited so long as it has a buffering ability, it is, for example, 5 mM or higher, preferably 10 mM or higher. When a buffer at such a concentration is used, content of the buffering ingredient in the dried composition is not particularly limited, but it is preferably in the range of 0.1 to 80 mass %.

Content of the L-glutamate oxidase in the aqueous composition is preferably 10 to 500 U/mL, more preferably 25 to 300 U/mL, in terms of the enzymatic activity per 1 mL. This is because a content in such a range provides high recovery rate in the drying step, and properties of the obtained dried composition favorable for handling. This is further because a content in such a range enables efficient drying with maintaining the high order structure of the protein.

Content of the disaccharide in the aqueous composition can be optionally determined so long as the effect of stabilizing L-glutamate oxidase can be obtained in an objective dried composition. For example, the concentration of the disaccharide in the aqueous composition may be 0.1 to 100 mg/mL. It is preferably 3 to 25 mg/mL, more preferably 5 to 15 mg/mL, in order to obtain favorable handling properties of the dried composition to be obtained.

The aqueous composition containing an L-glutamate oxidase and a disaccharide can be prepared at a temperature at which the L-glutamate oxidase is stable. Although such a temperature is, for example, 2 to 40° C., it can also be prepared at environmental temperature. It is preferred that the obtained aqueous composition is promptly subjected to the following drying step.

(Drying Step)

Subsequently, the obtained aqueous composition is subjected to the step for dehydration to obtain a dried composition. The dehydration can be performed according to a known method. Examples of the method include a method of precipitating contained ingredients from the aqueous composition containing an L-glutamate oxidase and a disaccharide using an organic solvent, and making them into dried powder, a spray-drying method of spraying the aqueous composition, and applying a hot wind to it to dry it, a lyophilization method of freezing the aqueous composition, and drying it under a reduced pressure, and so forth, but the method is not limited to these. The lyophilization method is preferred, since it hardly causes heat denaturation, and provides good solubility of the dried composition to be obtained.

At the time of the lyophilization, the aqueous composition obtained in the previous step is frozen. The temperature for freezing may be arbitrarily determined so long as the L-glutamate oxidase is stable, and is, for example, −90 to −10° C.

As the equipment for drying or lyophilization, conventional equipments can be used, and as the conditions, the conditions used for production of conventional enzyme preparations can be appropriately used. In the case of the lyophilization, degree of vacuum is not particularly limited, but may be, for example 1 to 200 Pa, preferably 5 to 130 Pa, and drying temperature may be 20 to 60° C.

[Use and Others]

(Method for Measuring Enzymatic Activity)

The enzymatic activity of the L-glutamate oxidase contained in the dried L-glutamate oxidase composition of the present invention (the activity that can convert 1 μmol of the substrate per 1 minute at 30° C. under the optimal conditions is defined as 1 U) can be measured by the oxygen electrode method or the MBTH method.

The oxygen electrode method is a method of adding a sample enzyme solution of unknown enzymatic activity to an L-glutamate substrate solution, measuring change of the oxygen concentration in the solution, and calculating rate of the oxygen consumption resulting from the reaction catalyzed by the L-glutamate oxidase to determine the enzymatic activity of the L-glutamate oxidase.

The MBTH method is a method for measuring an α-keto acid using 3-methyl-2-benzothiazolinone hydrazone hydrochloride monohydrate (MBTH) with the protocol shown below. By measuring α-ketoglutarate as the product of the reaction catalyzed by L-glutamate oxidase by this MBTH method, L-glutamate oxidase activity can be measured.

(1) Mix a 100 mM potassium phosphate buffer, pH 7.4 (0.7 mL), 300 U/mL of catalase (0.1 mL), and a 100 mM sodium L-glutamate standard solution (0.1 mL) to obtain a reaction mixture A.
(2) Heat the reaction mixture A (0.9 mL) at 30° C. for 5 minutes, and then add a sample enzyme solution of unknown enzymatic activity (0.1 mL) to the reaction mixture A to start the reaction.
(3) After the addition of the sample enzyme solution, allow the reaction at 30° C. for exactly 20 minutes, and then add 25% TCA (0.1 mL) to terminate the reaction.
(4) Add a 1.0 M acetate buffer, pH 5.0 (1.9 mL), and 0.1% MBTH aqueous solution (0.8 mL) to the solution in which the reaction was terminated, and allow the reaction at 50° C. for 30 minutes.
(5) Leave the solution at room temperature for 20 minutes, and then measure OD 316 nm of the solution with a spectrophotometer (single beam), of which zero point is calibrated with water as a control.
(6) Separately create a calibration curve using a standard α-ketoglutarate solution (1.0 mL) through the steps (3) and (4) mentioned above.

OD 316 nm of a solution obtained through the reactions of the steps (1) to (5) using a 20 mM potassium phosphate buffer, pH 7.4 (0.1 mL) instead of the sample enzyme solution as a control is subtracted from the OD 316 nm of the solution obtained with the sample enzyme solution, and amount of α-ketoglutarate generated in 20 minutes at 30° C. can be calculated on the basis of the difference.

(Use)

The dried L-glutamate oxidase composition obtained according to the present invention can be effectively used in an L-glutamic acid measurement kit and an enzyme sensor for measuring L-glutamate oxidase.

EXAMPLES

Hereafter, the present invention will be specifically explained with reference to examples. However, the present invention of course is not limited by the examples.

Example 1

Search for Compound Having L-Glutamate Oxidase-Stabilizing Effect

A solution of L-glutamate oxidase obtained by the method described in Non-patent document 1 in a 20 mM potassium phosphate buffer, pH 7.4 was adjusted to have an L-glutamate oxidase enzymatic activity per 1 mL of 400 U/mL. To this enzyme solution, 20 mg/mL solutions of lactose, which is a disaccharide, dextran 40, which is a polysaccharide, and mannitol, which is a sugar alcohol, dissolved in the same buffer were each added to obtain L-glutamate oxidase activity and concentration of each stabilizing agent in the mixture of 200 U/mL and 10 mg/mL, respectively. Each mixture was put into lyophilization vials in a volume of 1 mL each, and lyophilized. Five samples were prepared for each concentration.

The lyophilized products were stored at 37° C. for two weeks, and then dissolved with water so that the solution presumably had the enzymatic activity of 100 U/mL. The solution was further diluted with a 20 mM potassium phosphate buffer, pH 7.4 to have a presumed enzymatic activity of 10 U/mL, and the activity of the solution was measured by the oxygen electrode method.

TABLE 1

|  | Lactose | Dextran | Mannitol |
|---|---|---|---|
| Activity (U/mL) | 9.47 | 7.75 | 4.71 |
| Relative activity (%) | 101.5% | 83.1% | 50.5% |

The results of the experiment were as shown in Table 1. The reference for comparison used for calculation of the relative activity values of the enzyme was an average activity of samples stored at −40° C. after lyophilization under the aforementioned conditions. The average activity of the samples stored at −40° C. after the lyophilization was 9.33 (U/mL), and differences of the activity values and dispersion thereof were not observed for the added compounds.

In the composition to which lactose was added, decrease of the activity was not observed, and extremely favorable stability was observed. The stability was similarly confirmed in the ranges of L-glutamate oxidase activity of 100 to 300 U/mL and the final lactose concentration of 5 to 15 mg/mL in the aqueous composition before the lyophilization.

On the other hand, the residual activity ratio of the composition to which dextran 40 was added was 83.1%, and the stability was comparable to that obtainable by the methods for stabilizing carbohydrate-related enzymes using existing saccharides. The residual activity was confirmed with L-glutamate oxidase activities in the ranges of 100 to 300 U/mL, and final dextran 40 concentrations in the ranges of 5 to 15 mg/mL in the aqueous composition before the lyophilization, but any residual activity ratio exceeding the aforementioned value was not obtained.

In the composition to which mannitol was added, the activity was halved after the experiment, and it was found that the composition was unstable.

All the lyophilized products showed favorable handling properties, and did not show any properties that may constitute a barrier for industrial use thereof.

Example 2

Experiment for Long Term Stability of
L-Glutamate Oxidase

Long term stability of the obtained L-glutamate oxidase was examined.

A solution of L-glutamate oxidase obtained by the method described in WO2001/079503 in a 20 mM potassium phosphate buffer, pH 7.4 was adjusted to have an L-glutamate oxidase enzymatic activity per 1 mL of 25 U/mL and a lactose concentration of 7 mg/mL. This diluted solution was put into lyophilization vials in a volume of 1 mL each, and lyophilized. The lyophilized products were stored at −20° C., and the long term stability test was performed for eight years and seven months at most. The enzymatic activity was measured by the MBTH method.

TABLE 2

|  | Date | | | | | | |
| --- | --- | --- | --- | --- | --- | --- | --- |
|  | 2008 Mar. 11 | 2008 Jun. 10 | 2008 Sep. 22 | 2010 Aug. 7 | 2011 Jan. 10 | 2014 Jul. 7 | 2016 Oct. 14 |
| Activity (U/mL) | 9.73 | 9.63 | 9.65 | 10.29 | 10.00 | 9.44 | 9.65 |
| Relative activity (%) | 100 | 99.0 | 99.2 | 105.8 | 102.8 | 97.0 | 99.2 |

The results of the long term stability test were as shown in FIG. 1 and Table 2. The obtained compositions surprisingly showed the activity corresponding to 97% or more of the activity observed before the storage throughout the experiment, and showed the activity corresponding to 99% of the activity observed before the storage even after long term storage over 8 years.

INDUSTRIAL APPLICABILITY

The dried L-glutamate oxidase composition of the present invention shows such marked stability as has not been reported so far, and shows superior handling properties. The present invention provides an L-glutamate oxidase composition showing improved handling properties and improved stability.

The invention claimed is:

1. A dried L-glutamate oxidase composition, consisting of an L-glutamate oxidase and 0.5 to 50 mg of a disaccharide per 100 U of the L-glutamate oxidase.

2. The composition according to claim 1, which is a lyophilized product.

3. The composition according to claim 1, wherein the disaccharide is lactose.

4. The composition according to claim 1, wherein the L-glutamate oxidase is derived from *Streptomyces* sp. X-119-6 with an accession number ATCC 39343.

5. The dried L-glutamate composition according to claim 1, which shows, after storage for one year under frozen conditions of −20° C., an activity value of the enzyme corresponding to 95% or more of the activity value observed before the storage as measured by a 3-methyl-2-benzothiazolinone hydrazone hydrochloride monohydrate (MBTH) method.

6. The composition according to claim 5, wherein the disaccharide is lactose.

7. A method for producing a dried L-glutamate oxidase composition which consists of an L-glutamate oxidase and a disaccharide, the method comprising:
 preparing an aqueous composition consisting of an L-glutamate oxidase and a disaccharide,
 dehydrating the prepared aqueous composition to obtain a dried composition,
 storing the dried composition for at least 4 weeks,
 and measuring an enzymatic activity of the stored composition.

8. The method according to claim 7, wherein the dehydrating step is carried out by lyophilizing to obtain a lyophilized product.

9. The method according to claim 7, wherein the disaccharide is lactose.

10. The method according to claim 7, wherein the aqueous composition consists of 0.5 to 50 mg of the disaccharide per 100 U of the L-glutamate oxidase.

11. The method according to claim 7, further comprising a prior step of producing L-glutamate oxidase from a transformed *Escherichia coli* or actinomycete with a foreign L-glutamate oxidase gene.

12. The method according to claim 7, wherein the preparing step comprises buffering the aqueous composition to a pH range of 6.5 to 8.0.

13. The method according to claim 12, wherein the concentration of a buffering agent in the buffered aqueous composition is 100 mM or lower.

14. The method according to claim 7, wherein the storing step is continued for at least one year.

15. The method according to claim 7, wherein the measuring step is to confirm that the enzymatic activity of the stored composition is 95% or more of the enzymatic activity observed before the storing step as measured by the MBTH method.

* * * * *